United States Patent [19]

Sato et al.

[11] Patent Number: 5,177,232

[45] Date of Patent: Jan. 5, 1993

[54] METHOD FOR CHEMICALLY MODIFYING A METAL COMPLEX

[75] Inventors: Mitsunobu Sato, Chiba; Shigenobu Yano, Nara; Ryuichi Kitayama, Sagamihara; Katsuo Komiya, Ayase, all of Japan

[73] Assignee: Tosoh Corporation, Shinnanyo, Japan

[21] Appl. No.: 727,590

[22] Filed: Jul. 9, 1991

Related U.S. Application Data

[62] Division of Ser. No. 491,234, Mar. 9, 1990, Pat. No. 5,061,816.

[30] Foreign Application Priority Data

Mar. 13, 1990 [JP] Japan .................................. 1-57778

[51] Int. Cl.$^5$ ...................... C07F 15/06; C07C 229/00
[52] U.S. Cl. .................................. 556/148; 556/138; 556/146; 560/169; 560/171; 585/839; 585/856
[58] Field of Search ...................... 556/138, 146, 148; 585/839, 856; 560/169, 171

[56] References Cited

PUBLICATIONS

Sam et al., J. Amer. Chem. Soc., vol. 94, No. 11, pp. 4024-4025 (1972).
Sam et al., J. Amer. Chem. Soc., vol. 96, No. 7, pp. 2252-2253 (1974).
Liotta et al., J. Amer. Chem. Soc., vol. 96, No. 7, pp. 2250-2252 (1974).
Nishikiori et al., Bull. Chem. Soc. Jpn., vol. 53, No. 8, pp. 2236-2240 (1980).
Taura, Inorg. Chem., vol. 27, No. 16, pp. 2845-2847 (1988).

*Primary Examiner*—Jose G. Bees
*Assistant Examiner*—Porfirio Nazario
*Attorney, Agent, or Firm*—Oblon, Spivak, McClelland, Maier & Neustadt

[57] ABSTRACT

A method for chemically modifying an anionic metal complex, by obtaining from an anionic metal complex insoluble in a non-aqueous solvent and a clathrate compound a clathrate complex thereof with a counter cation of said metal complex, which is soluble in a non-aqueous solvent, and then reacting functional groups of the metal complex, which are not concerned with the coordination of said metal complex, with an organic reagent in the presence of a reaction assistant.

The central metal from the chemically modified metal complex may then be removed.

6 Claims, No Drawings ligand exchange resin) after the completion of the above reaction of the functional groups which are not concerned with the coordination.

As described in the foregoing, according to the present invention, it is possible to solublize a metal complex which used to be hardly modified, in a nonaqueous solvent by using a compound having a clathrate inclusion ability and to readily selectively chemically modifying only the functional groups which are not concerned with the coordination, and it is possible to obtain a chemically modified ligand by freeing the metal and the ligand of the metal complex.

Now, the present invention will be described in further detail with reference to Examples. However, it should be understood that the present invention is by no means restricted to such specific Examples.

Hereinafter, dhpta represents 1,3-diamino-2-hydroxypropane tetraacetic acid, Ac represents acetyl, and Suc represents succinyl.

EXAMPLE 1

Acetylation reaction of K[Co(dhpta)]

0.4 g (0.96 mmol) of K[Co(dhpta)] was dissolved in 20 ml of an acetonitrile solution containing 0.4 g (1.06 mmol) of Criptand 222. Then, 0.12 g (0.98 mmol) of N,N-dimethylaminopyridine and 0.5 g (5 mmol) of acetic anhydride were sequentially added thereto, and the mixture was stirred at room temperature for 3 hours.

The product was obtained in the form of precipitates. The precipitates were collected to obtain an acetylated complex.

This complex was dissolved in water, and the aqueous solution was passed through a cation exchange resin (Dowex 50 w ×2, K+) and subjected to gel permeation and reprecipitation from methanol to obtain 440 mg (yield: 80%) of K[Co(Ac-dhpta)].

From the $^{13}$C-NMR analysis, the product was confirmed to be an acetylated product, as the peaks of carbonyl carbon of an acetyl group at 171.8 ppm and methyl carbon of an acetyl group at 20.2 ppm were observed anew.

EXAMPLE 2

Reaction of K[Co(dhpta)] with succinic anhydride

In the same manner as in Example 1, 380 mg (yield: 80%) of K[Co(Suc-dhpta)] was obtained using 0.4 g (0.96 mol) of K[Co(dhpta)], 0.3 g (2 mmol) of succinic anhydride, 0.12 g (0.98 mmol) of N,N-dimethylaminopyridine and 15 ml of CH$_3$CN.

From the $^{13}$C-NMR analysis, the product was confirmed to be a succinyl-modified product as peaks of carbonyl carbon and carboxyl carbon were observed anew at 173.2 ppm and 178.9 ppm, respectively.

EXAMPLE 3

Recovery of dhpta-OAc from the Co complex

A product obtained by acetylating K[Co(dhpta)] in the same manner as in Example 1, was added to a mixture of Na$_2$S.H$_2$O (20.0 g) and KOH (4 g) heated to 80° C. Further, NaOH (50 g) was added thereto, and the mixture was heated at 100° C. for a few minutes. Then, benzene (100 ml) was added thereto, and the mixture was refluxed for 30 minutes under heating. The mixture was cooled. Then, the benzene solution was poured to KOH pellets. From the benzene solution, dhpta-OAc (hydrochloride) was extracted with a concentrated hydrochloric acid aqueous solution, and the extract was concentrated under reduced pressure.

The product was confirmed to be dhpta-OAc from the IR analysis, as an absorption by an acetyl group was observed at 1,750 cm$^{-1}$.

We claim:

1. A method for producing a chemically modified coordination compound, which comprises removing by chemical means the central metal from the chemically modified metal complex obtained from an anionic metal complex insoluble in a non-aqueous solvent and a clathrate compound, a clathrate complex of said clathrate compound with a counter of cation of said anionic metal complex, which is soluble in a non-aqueous solvent, and then reacting functional groups of said metal complex, which are not concerned with the coordination of said metal complex, with an organic reagent in the presence of a reaction assistant, wherein the functional groups which are not concerned with the coordination of said metal complex, are hydroxyl groups, amino groups, ketone groups, epoxy groups, isocyanato groups, ester groups or amido groups.

2. The method according to claim 1, wherein the clathrate compound is a counter cation-capturing agent.

3. The method according to claim 1, wherein the clathrate compound is a crown ether or a criptand.

4. The method according to claim 1, wherein the nonaqueous solvent is an alcohol, an aprotic polar solvent or an aprotic non-polar solvent.

5. The method according to claim 1, wherein the organic reagent is an acid anhydride, a lactone, a lactam, an isocyanate, an amino compound or a carboxy compound.

6. The method according to claim 1, wherein the reaction assistant is an organic base in the case of a reaction of a hydroxyl group with an acid halide or a hydroxyl group with an acid anhydride, or dicyclohexylcarbodiimide in the case of condensation of an amine group with a carboxyl group.

* * * * *

METHOD FOR CHEMICALLY MODIFYING A METAL COMPLEX

This is a division of application Ser. No. 07/491,234 filed on Mar. 9, 1990, now U.S. Pat. No. 5,061,816.

The present invention relates to a method for chemically modifying a metal complex. More particularly, the present invention relates to a method whereby the chemical modification reaction of a metal complex which used to be hardly chemically modified, can efficiently be conducted.

Heretofore a method has been known in which a clathrate inclusion phenomenon is utilized to efficiently conduct an organic reaction. Some instances have been known in which various inorganic reactants are made soluble in non-aqueous solvents by means of clathrate compounds to conduct various reactions.

For example, Simmons has found that an oxidation reaction as shown by the formula (I) can be conducted smoothly by solublizing potassium permanganate in benzene by means of dicyclohexyl-18-crown (D. J. Sam. H. E. Simmons, JACS., 94,4020(1972)).

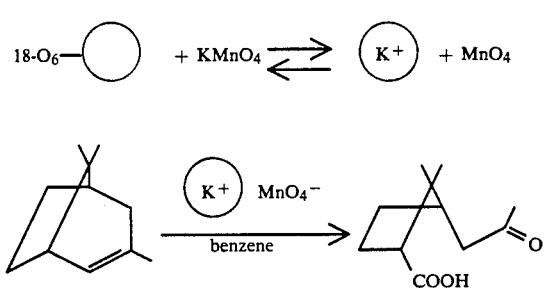

(I)

Further, this is utilized also for applications to a nucleophilic substitution reaction, an esterification reaction, an anion polymerization, a decarboxylation reaction, etc. These applications are described in "Crown Ether Chemistry" (Kagaku Zokan, 74, (1978) Published by Kagakudojin).

On the other hand, no instance has been known wherein such a clathrate inclusion phenomenon is utilized for chemical modification of a metal complex itself. Also with respect to the utilization of the clathrate inclusion phenomenon for solublizing a complex to a non-aqueous solvent, a recent report by T. Taura is the only one. Namely, this report is concerned with a case wherein an anionic metal complex is solublized in a non-aqueous solvent by means of a clathrate compound, whereupon the interaction between the complex and the solvent is studied (T. Taura, Inorg. Chem., 1988, 27, 2845). However, also in this study, no consideration is given for application to an organic reaction such as chemical modification, and the ligand used was of a non-reactive type.

In order to fix a metal complex to various carriers such as a carrier for liquid chromatography, a membrane and a glass surface by a covalent bond, it is necessary to chemically modify the ligand portion of the complex. However, it is practically impossible to chemically modify a metal complex which is insoluble in a non-aqueous solvent. Therefore, it used to be common to conduct the modification at the stage of a ligand prior to the formation of the complex, and the application in this field has been left behind.

The present inventors have conducted extensive studies to expand the utilization and applicability of metal complexes by selectively conducting the chemical modification without changing the coordination function of ligands.

Firstly, it was attempted to conduct organic chemical reactions of metal complexes particularly in non-aqueous solvents, but the complexes exhibited no substantial reaction, and all the attempts ended in vain with recovery of the starting materials. Further, it was attempted to selectively chemically modify only the functional groups which were not concerned with the coordination among ligands as a pretreatment, but such chemical modification was found to be difficult requiring a long process.

From a further study, it has been found possible to conduct such a chemical modification reaction simply and efficiently by using a crown compound or a criptand which was not used before. The present invention has been accomplished on the basis of this discovery.

Thus, the present invention provides a method for chemically modifying a metal complex, which comprises obtaining, from a metal complex insoluble in a non-aqueous solvent and a clathrate compound, a clathrate complex of said clathrate compound with a counter cation of said metal complex, which is soluble in a non-aqueous solvent, and then reacting functional groups of said metal complex, which are not concerned with the coordination of said metal complex, with an organic reagent in the presence of a reaction assistant.

Further, the present invention provides a method for producing a chemically modified coordination compound, which comprises removing the central metal of the chemically modified metal complex obtained by the above chemical modification method.

Now, the present invention will be described in further detail with reference to the preferred embodiments.

In the present invention, the chemical modification is meant for a modification such as acetylation, succinyl-modification, amination or a benzoyl-modification.

The clathrate compound used in the present invention is a counter cation-capturing agent such as a crown ether or a criptand.

The non-aqueous solvent may suitably be selected depending upon the reaction or the metal complex. It is selected usually from the group consisting of alcohols, aprotic polar solvents and aprotic non-polar solvents.

The functional groups which are not concerned with the coordination of the metal complex may be hydroxyl groups, amino groups, ketone groups, epoxy groups, isocyanate groups, ester groups or amido groups.

As the organic reagent, a usual agent for an organic reaction is used. For example, it may be an acid anhydride, a lactone, a lactum, an isocyanate, an amino compound or a carboxy compound.

The reaction assistant may be, for example, a reagent required for a usual organic chemical reaction, such as an organic base in the case of a reaction of a hydroxyl group with an acid halide or a hydroxyl group with an acid anhydride, or dicyclohexylcarbodiimide (DCC) in the case of condensation of an amino group with a carboxyl group.

Further, it has been found that by employing a metal having a low stability constant as the central metal of the metal complex, it is possible to isolate a modified ligand by an operation or reaction for removing the central metal (for example, by a method by means of a